(12) United States Patent
Rivas P.

(10) Patent No.: US 7,032,449 B2
(45) Date of Patent: Apr. 25, 2006

(54) MEASUREMENT OF FLUID PROPERTIES IN VESSEL AND SENSOR FOR SAME

(75) Inventor: Oswaldo A. Rivas P., Edo. Miranda (VE)

(73) Assignee: Intevep, S.A., Caracas (VE)

(*) Notice: Subject to any disclaimer, the term of this patent is extended or adjusted under 35 U.S.C. 154(b) by 0 days.

(21) Appl. No.: 10/891,700

(22) Filed: Jul. 14, 2004

(65) Prior Publication Data

US 2006/0010962 A1 Jan. 19, 2006

(51) Int. Cl.
*G01N 9/12* (2006.01)

(52) U.S. Cl. .......................................... 73/438; 73/299

(58) Field of Classification Search ............. 73/290 R, 73/304 R, 304 C, 438, 299
See application file for complete search history.

(56) References Cited

U.S. PATENT DOCUMENTS

| | | | | |
|---|---|---|---|---|
| 4,375,764 A | * | 3/1983 | Lawford et al. | 73/301 |
| 4,425,787 A | * | 1/1984 | Saraf | 73/32 R |
| 4,471,656 A | * | 9/1984 | Sanders et al. | 73/438 |
| 4,625,553 A | * | 12/1986 | Charter | 73/438 |
| 4,747,062 A | * | 5/1988 | Esau | 702/55 |
| 4,967,593 A | * | 11/1990 | McQueen | 73/295 |
| 5,088,317 A | * | 2/1992 | Jensen | 73/49.2 |
| 5,105,662 A | * | 4/1992 | Marsh et al. | 73/299 |
| 5,351,725 A | * | 10/1994 | Suthergreen et al. | 141/1 |
| 5,400,651 A | * | 3/1995 | Welch | 73/290 R |
| 5,686,658 A | * | 11/1997 | Boren | 73/49.2 |
| 5,827,963 A | * | 10/1998 | Selegatto et al. | 73/438 |
| 5,841,020 A | * | 11/1998 | Guelich | 73/19.12 |
| 6,257,070 B1 | | 7/2001 | Giallorenzo et al. | |
| 6,282,953 B1 | * | 9/2001 | Benjey | 73/438 |
| 6,687,643 B1 | * | 2/2004 | Cason, Jr. | 702/137 |

* cited by examiner

*Primary Examiner*—Hezron Williams
*Assistant Examiner*—John Fitzgerald
(74) *Attorney, Agent, or Firm*—Bachman & LaPointe, P.C.

(57) ABSTRACT

A sensor for measuring properties of a fluid in a vessel, includes a sensor mount adapted to mount within a wall of a vessel; a sensor body extending substantially vertically from the sensor mount; and a plurality of sensors spaced vertically along the sensor body, whereby at least one of level, density, temperature and pressure of fluid in the vessel can be measured.

10 Claims, 1 Drawing Sheet

MEASUREMENT OF FLUID PROPERTIES IN VESSEL AND SENSOR FOR SAME

BACKGROUND OF THE INVENTION

The invention relates to measurement of fluid properties within a vessel, and more particularly to a sensor for use in measuring fluid properties within a vessel.

Measurement of fluid property such as fluid density, temperature, pressure, level and the like within vessels is frequently needed for various industrial processes.

Sensors must be positioned properly to determine various readings relative to the fluid, and such sensors frequently must be positioned to extend through the side wall of the vessel containing the fluid.

U.S. Pat. No. 6,257,070 discloses a vessel having various sensors positioned through perforations of the vessel wall. FIG. 1 shows a similar vessel 1, which includes a level sensor port 2 and a vapor pressure port 6, and in which four additional ports 3, 4, 5 and 7 must be made. For these ports, perforations must be made through vessel 1, in order to properly position the desired sensors. While the device disclosed in the aforesaid U.S. Pat. No. 6,257,070 functions to provide the desired measurements, it would be preferred to avoid having to make the five extra perforations through the vessel wall.

It is therefore the primary object of the present invention to provide a sensor and vessel including a sensor wherein such measurements can be obtained from sensors positioned as desired without the need for extra perforations of the vessel wall.

Other objects and advantages of the present invention will appear herein below.

SUMMARY OF THE INVENTION

In accordance with the present invention, the foregoing objects and advantages have been readily attained.

According to the invention, a sensor is provided for measuring properties of a fluid in a vessel, which sensor comprises; a sensor mount adapted to mount within a wall of a vessel; a sensor body extending substantially vertically from the sensor mount; and a plurality of sensors spaced vertically along the sensor body, whereby at least one of level, density, temperature and pressure of fluid in the vessel can be measured.

In further accordance with the invention, a vessel and sensor are provided for measuring properties of fluid in the vessel, comprising; a vessel having a sidewall and a port; and a sensor comprising a sensor mount adapted to mount within the port of the vessel; a sensor body extending substantially vertically from the sensor mount; and a plurality of sensors spaced vertically along the sensor body, whereby at least one of level, density, temperature and pressure of fluid in the vessel can be measured.

BRIEF DESCRIPTION OF THE DRAWING

A detailed description of preferred embodiments of the present invention follows, with reference to the attached drawings, wherein.

DETAILED DESCRIPTION

The invention relates to measurement of fluid properties within a vessel and, more particularly, to a sensor for measuring such fluid properties which does not require additional perforations through the vessel wall during installation.

Figures 1, 2:
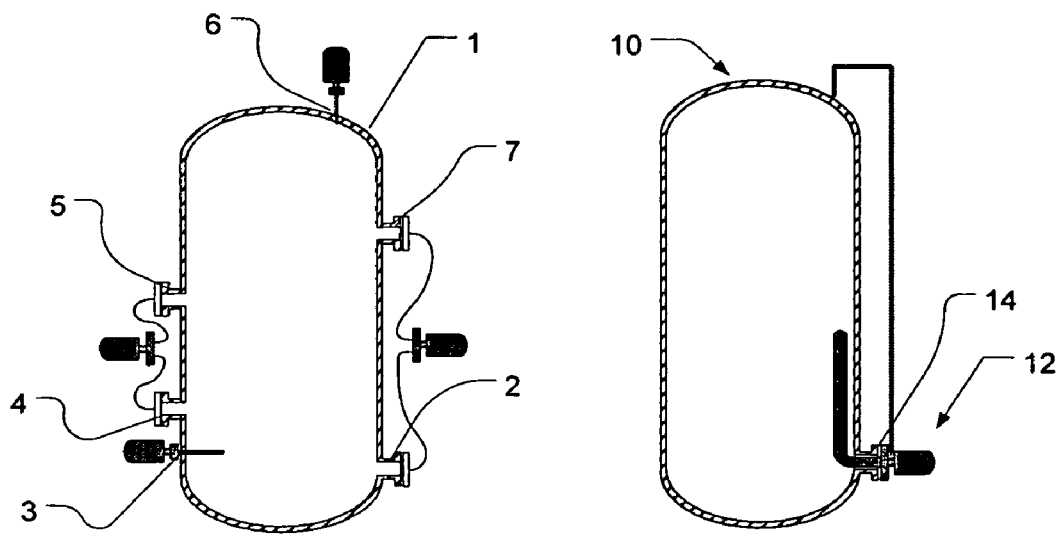
FIG. 1 illustrates a prior art vessel with sensors.
FIG. 2 illustrates a vessel and sensor in accordance with the present invention.

Referring to FIG. 2, a combination of vessel 10 and sensor 12 are shown. Vessel 10 is typically any vessel used to receive and/or store a fluid, the properties of which are desirable to be measured. One particular example of such a fluid includes hydrocarbon products in various stages of processing and/or refining.

In accordance with the invention, vessel 10 includes a level sensor port 14, and sensor 12 in accordance with the present invention is advantageously mounted within port 14 and provides for measurement of fluid density, fluid level, fluid temperature, fluid pressure and the like, without the need for the additional perforations or ports to be positioned within vessel 10, which is in clear contrast to the prior art configuration of FIG. 1.

Figure 3:
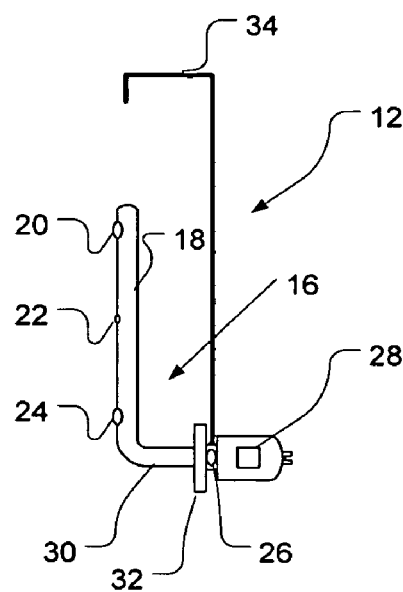
FIG. 3 illustrates in greater detail the structure of a sensor in accordance with the present invention.

Turning to FIG. 3, an enlarged view of sensor 12 in accordance with the present invention is provided. According to the invention, sensor 12 includes a sensor mount 16 adapted for mounting within a port of vessel 10, preferably for mounting within level sensor port 14 of vessel 10. Sensor 12 further includes a substantially vertical portion 18, and a plurality of sensors 20, 22, 24, 26 positioned thereon.

Sensors 20, 22, 24 and 26 are advantageously positioned along portion 18, preferably spaced vertically along same. These sensors can be any type of sensor well known to persons of ordinary skill in the art for measuring the quantities identified. Portion 18 is identified as being substantially vertically extending. By this it is meant that portion 18 extends substantially along the pressure gradient within the vessel. Usually this will be substantially vertical with respect to the horizon. Of course, portion 18 could be positioned deliberately or otherwise at an angle with respect to the vertical. So long as this angle is known, or the resulting vertical distance between sensors is known, the device can be used to measure fluid properties as described herein, well within the broad scope of the present invention. A processor unit 28 can be communicated with the sensors and provided with proper programming to take measurements from the sensors and determine fluid density, fluid temperature, fluid pressure and fluid level within the vessel.

According to the invention, sensors 20, 22, 24 and 26 are advantageously positioned as follows.

Sensors 20, 22, 24, 26 preferably include a middle differential pressure sensor 20, a high differential pressure sensor 24, a temperature sensor 22 and a low pressure sensor 26. Middle differential pressure sensor 20 and high differential pressure sensor 24 are advantageously mounted and vertically spaced along substantially vertical portion 18. These sensors are mounted a known vertical distance from each other, and this vertical distance can advantageously be selected to be proportional to the height of the vessel, whereby substantially accurate measurements can be obtained. With this known vertical spacing, pressure measurements at sensors 20 and 24 can advantageously be utilized by processor 28 to determine density of fluid within the vessel. This density can advantageously be corrected for temperature using measurements from temperature sensor 22, and can also be corrected for ambient pressure or vapor pressure using measurements from low pressure sensor 26. Once fluid density has been determined, fluid level within the vessel can be determined based upon measurements from high differential pressure sensor 24 and the determined density.

In addition, the processor in accordance with the present invention can advantageously be adapted to correct density measurements based upon average fluid temperature and measurements of the vapor pressure.

As shown, sensors 20, 22 and 24 are advantageously positioned substantially vertically spaced along substantially vertical portion 18. In this regard, temperature sensor 22 is advantageously positioned substantially at a mid point between sensors 20 and 24. Furthermore, sensor 12 further includes a substantially horizontal portion 30 which is adapted for mounting within a port of the vessel, preferably for mounting within already-existing port 14. Sensor 12 can further be provided having a flange 32 for positioning against an edge of port 14 of vessel 10, and for stabilizing sensor 12 in the mounted position.

Sensor 12 in accordance with the present invention can further be provided having a common pressure connection port 34 which is advantageously commonly connected to all sensors of pressure and points of measurement of existent vapor pressure in the upper portions of closed containers. When measuring open-top containers, this port can remain without connection for ambient pressure measurement.

It should be appreciated that sensor 12 in accordance with the present invention advantageously has middle differential pressure sensor 20 mounted vertically highest along vertical portion 18, with high differential pressure sensor 24 being mounted below sensor 20, and with temperature sensor 22 positioned at a substantial mid-point between same.

It should also be appreciated that low pressure sensor 26 is advantageously positioned for vapor pressure measurement in closed containers or exposure to ambient conditions outside of the vessel to be measured in open-top containers.

Finally, it should also be appreciated that the processor unit in accordance with the present invention can be any type of processor hardware such as a desktop computer, on-board processing capability, and the like, and that such processing hardware can be adapted to the various functions set forth above utilizing various software and/or programming techniques which are well known to a person of ordinary skill in the art.

Based upon the foregoing, it should be appreciated that a sensor has been provided which readily accomplishes the aforesaid objectives. That is, the sensor properly positions various different sensors at vertically spaced positions within a vessel, without requiring additional perforations through the walls of the vessel.

It is also to be understood that this invention is not limited to the illustrations described and shown herein, which are deemed to be merely illustrative of the best mode of carrying out the invention, and which are susceptible to modification in form, size, arrangement of parts and details of operation. The invention rather is intended to encompass all such modifications which are within its spirit and scope of the appended claims.

What is claimed is:

1. A sensor for measuring properties of a fluid in a vessel, comprising:
    a sensor mount adapted to mount within a wall of a vessel;
    a sensor body extending substantially vertically from the sensor mount; and
    a plurality of sensors spaced vertically along the sensor body, the plurality of sensors include a middle differential pressure sensor, a high differential pressure sensor, a temperature sensor and a low pressure sensor, wherein the plurality of sensors are mounted on the sensor body from vertically highest position down in the following order: middle differential pressure sensor, temperature sensor, high differential pressure sensor and low pressure sensor.

2. The sensor of claim 1, wherein the sensor mount comprises a substantially horizontal portion adapted to extend through a port of the vessel.

3. The sensor of claim 1, further comprising a processor communicated with the plurality of sensors and adapted to determine fluid density from the middle differential pressure sensor and the high differential pressure sensor and spacing between same.

4. The sensor of claim 3, wherein the processor is further adapted to correct the density measurement based upon average fluid temperature and vapor pressure measurements.

5. The sensor of claim 3, wherein the processor is further adapted to determine fluid level based upon fluid density and pressure from the high differential pressure sensor.

6. A vessel and sensor for measuring properties of fluid in the vessel, comprising:
    a vessel having a side wall and a port; and
    a sensor comprising:
    a sensor mount adapted to mount within the port of the vessel;
    a sensor body extending substantially vertically from the sensor mount; and
    a plurality of sensors spaced vertically along the sensor body, the plurality of sensors include a middle differential pressure sensor, a high differential pressure sensor, a temperature sensor and a low pressure sensor, wherein the plurality of sensors are mounted on the sensor body from vertically highest position down in the following order: middle differential pressure sensor, temperature sensor, high differential pressure sensor and low pressure sensor.

7. The apparatus of claim 6, wherein the sensor mount comprises a substantially horizontal portion adapted to extend through the port of the vessel.

8. The apparatus of claim 6, further comprising a processor communicated with the plurality of sensors and adapted to determine fluid density from the middle differential pressure sensor and the high differential pressure sensor and spacing between same.

9. The apparatus of claim 8, wherein the processor is further adapted to correct the density measurement based upon average fluid temperature and vapor pressure measurements.

10. The apparatus of claim 8, wherein the processor is further adapted to determine fluid level based upon fluid density and pressure from the high differential pressure sensor.

* * * * *